(12) United States Patent
Kominsky et al.

(10) Patent No.: US 7,758,813 B2
(45) Date of Patent: Jul. 20, 2010

(54) APPARATUS AND METHOD FOR SAMPLING OF AIRBORNE ASBESTOS AND OTHER PARTICLES RELEASED FROM A SURFACE

(75) Inventors: John R. Kominsky, Hebron, KY (US); Fred D. Hall, Cincinnati, OH (US)

(73) Assignee: Environmental Quality Management, Inc., Cincinnati, OH (US)

( * ) Notice: Subject to any disclaimer, the term of this patent is extended or adjusted under 35 U.S.C. 154(b) by 243 days.

(21) Appl. No.: 11/966,069

(22) Filed: Dec. 28, 2007

(65) Prior Publication Data

US 2009/0169435 A1 Jul. 2, 2009

(51) Int. Cl.
*B01L 3/00* (2006.01)
(52) U.S. Cl. .......................................... 422/99; 422/55
(58) Field of Classification Search .................. 422/99; 405/128.1, 128.15, 128.2, 128.25, 128.3, 405/128.35, 128.4, 128.45, 128.5, 128.55, 405/128.6, 128.65, 128.7, 128.75, 128.8, 405/128.85, 128.9
See application file for complete search history.

(56) References Cited

U.S. PATENT DOCUMENTS

| | | | | | |
|---|---|---|---|---|---|
| 1,611,786 | A | * | 12/1926 | Serva | ........................... 15/346 |
| 4,333,205 | A | * | 6/1982 | Woodward et al. | ............ 15/345 |
| 4,940,327 | A | | 7/1990 | Lilienfeld | |
| 5,457,848 | A | * | 10/1995 | Miwa | ........................... 15/346 |
| 5,647,092 | A | * | 7/1997 | Miwa | ........................... 15/346 |
| 5,867,860 | A | * | 2/1999 | Harris | ........................... 15/320 |
| 5,901,411 | A | * | 5/1999 | Hato et al. | .................... 15/381 |
| 6,005,662 | A | | 12/1999 | Ence | |
| 6,512,583 | B1 | | 1/2003 | Ence | |
| 6,571,421 | B1 | * | 6/2003 | Sham et al. | .................... 15/320 |
| 6,785,933 | B2 | * | 9/2004 | Kim et al. | ....................... 15/364 |
| 7,386,915 | B2 | * | 6/2008 | Blocker et al. | ................. 15/331 |
| 2005/0071946 | A1 | * | 4/2005 | Hafling et al. | ................ 15/352 |
| 2006/0130272 | A1 | * | 6/2006 | Oh et al. | ........................ 15/380 |

* cited by examiner

*Primary Examiner*—Jill Warden
*Assistant Examiner*—Charles Hammond
(74) *Attorney, Agent, or Firm*—Wood, Herron & Evans, LLP

(57) ABSTRACT

A sampling apparatus includes a housing defining a test chamber with an opening for contacting a test surface to expose at least a portion the test surface to the test chamber. A movable agitator within the test chamber contacts the test surface and agitates the test surface to release material from the test surface. The apparatus further includes an inlet and an outlet communicating with the test chamber and defining an air flow path through the chamber. At least one sample cassette may be supported near the outlet to collect a sample from the air flow, including material released from the surface into the test chamber.

9 Claims, 5 Drawing Sheets ated by the motor causes the agitator to move in oppo-
APPARATUS AND METHOD FOR SAMPLING OF AIRBORNE ASBESTOS AND OTHER PARTICLES RELEASED FROM A SURFACE This invention was made with government support under EPA Contract No. 68-C-00-186 awarded by the U.S. Environmental Protection Agency. The government has certain rights in the invention.

TECHNICAL FIELD

The present invention relates generally to environmental test devices, and more particularly to apparatus and methods for sampling of airborne particles released from a surface.

BACKGROUND

Asbestos is a naturally occurring fibrous material that has been mined and incorporated into more than 3,000 commercial products, including building materials and non-building related products. Asbestos and other mineral fibers may be present as introduced contamination in soils, or as settled dust on various horizontal surfaces in buildings. Exposure to asbestos fibers from natural sources or from activities using asbestos-containing materials can produce debilitating health effects in humans. Asbestos aerosolization, or releasability, is the potential for fibrous asbestos structures that are present in a material or on a solid surface to become airborne when the source is disturbed by human activities or natural forces. The magnitude of the airborne concentration that can be generated from the release of asbestos is a function of the concentration of asbestos at the source, certain properties of the source matrix, the nature of the activity causing the source to be disturbed, and local environmental conditions.

Conventional testing methods for repeatable and representative measurement of asbestos or other particle aerosolization from materials (e.g., soil) are not suitable for field use. These conventional methods require removal and transport of the source matrix (e.g., soil), thereby potentially altering the physical characteristics of the matrix and subsequent aerosolization.

It is desirable to be able to determine repeatable and representative asbestos or other particle aerosolization concentrations from soil in-situ. Risk management decisions would be greatly enhanced by knowing the level of airborne asbestos or other particles that are expected when asbestos-containing sources are disturbed by specific human activities or natural forces under defined environmental conditions.

SUMMARY

The present invention provides a sampling apparatus and methods for sampling asbestos or other particles released from a material or a surface that overcome drawbacks of prior apparatus and methods for sampling particles released from a material or a surface, such as those described above. In one embodiment, an apparatus for sampling asbestos or other particles released from a surface includes a housing having at least one sidewall defining a test chamber. The test chamber includes an opening that is adapted to confront a surface to be tested, so that a portion of the surface is exposed to the test chamber. The apparatus further includes a movable agitator disposed within the test chamber. The agitator contacts the test surface and thereby agitates the test surface as it moves within the test chamber.

The apparatus also includes an inlet and an outlet, both communicating with the test chamber to define an air flow path through the test chamber. As air flows through the test chamber, asbestos or other particles released from the test surface by movement of the agitator become entrained in the air flow and are moved toward the outlet. One or more sample cassettes are provided near the outlet to obtain samples of the released asbestos or other particles for subsequent analysis. The apparatus thus permits in-situ collection of a sample of asbestos or other particles released from a test surface without the need for additional processing which might otherwise affect the physical characteristics of the sample matrix, e.g., soil. In another aspect, other sampling apparatus (e.g., optical particle counters) may be used to collect and analyze particles.

In one aspect, the apparatus may further include a fan communicating with the inlet to provide a flow of air through the test chamber, between the inlet and the outlet. The speed of the fan may be adjustable to vary the flow rate of air through the test chamber.

In another aspect, the agitator may include one or more tines adapted to contact the test surface. The agitator may also be coupled to an actuator that is adapted to repeatedly move the agitator along a predetermined path within the test chamber to thereby facilitate the release of material from the test surface. In one embodiment, the actuator may include a threaded rod and a motor coupled to the threaded rod, whereby rotation of the threaded rod in opposite angular directions by the motor causes the agitator to move in opposite linear directions.

In another aspect, a method of sampling airborne asbestos or other particles released from a test surface includes exposing at least a portion of the test surface to a test chamber, agitating the portion of the test surface within the test chamber to release material of the test surface, providing a flow of air across the test surface, and collecting a sample of the air from the test chamber. In one embodiment, separate sample cassettes are used to collect samples of the air substantially simultaneously. One of the cassettes may then be examined while the test surface is still exposed to the test chamber, to evaluate the quality of the collected sample. If the collected sample is determined to be insufficient, the previously collected samples may be discarded and a new test may be run, using different test parameters if needed.

In one embodiment, the flow of air across the test surface is provided while the test surface is agitated. In another embodiment, the test surface is agitated while samples are collected.

By virtue of the foregoing, there are thus provided a sampling apparatus and methods for sampling asbestos or other particles released from a surface that overcome drawbacks of prior apparatus and methods for sampling asbestos or other particles released from a surface. These and other objects and advantages of the present invention shall be made apparent from the accompanying drawings and the description thereof.

DETAILED DESCRIPTION

Figure 1:
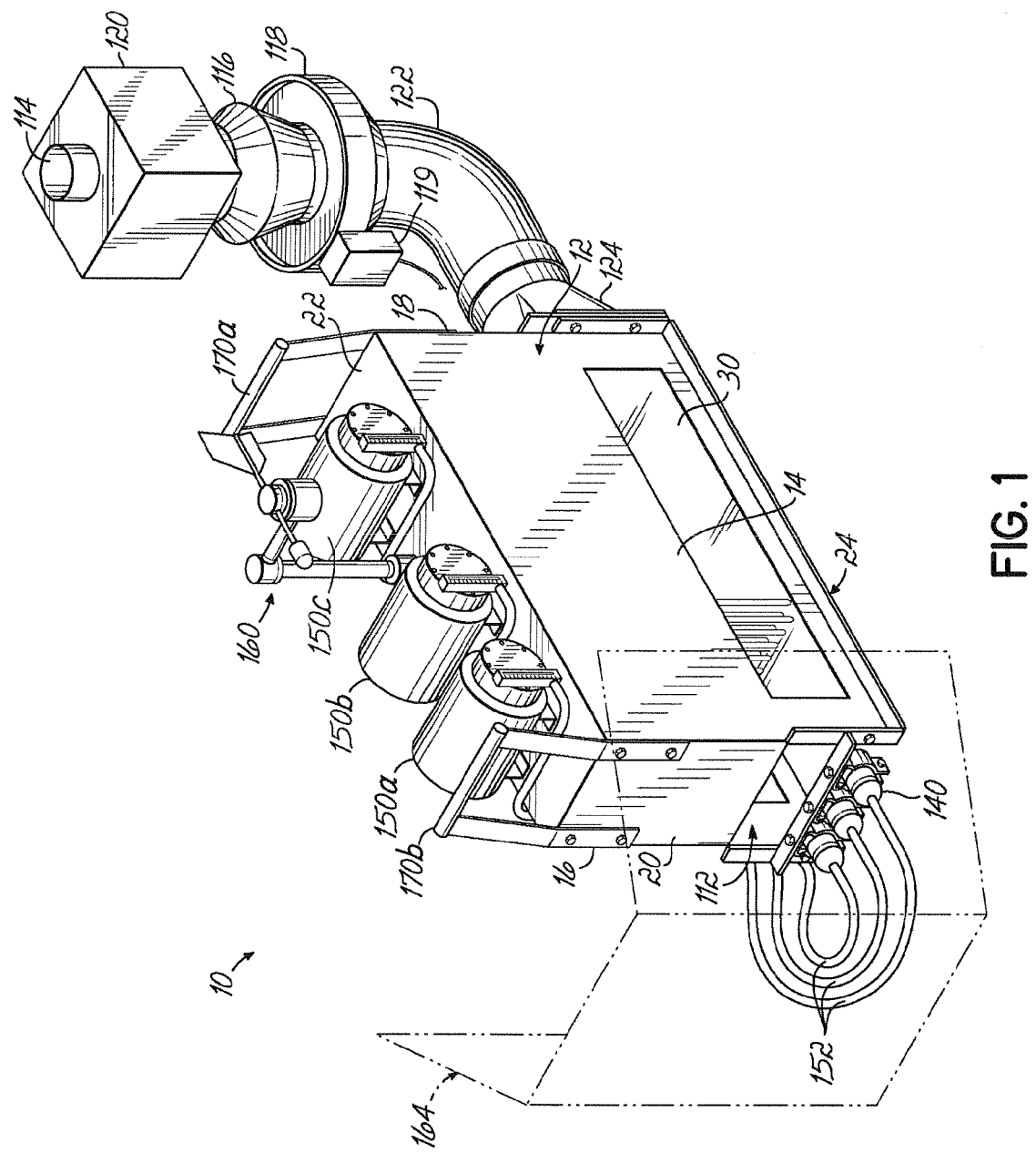
FIG. 1 is a perspective view of an exemplary apparatus for in-situ sampling of airborne materials released from a test surface, in accordance with the principles of the present disclosure.
Figure 2:
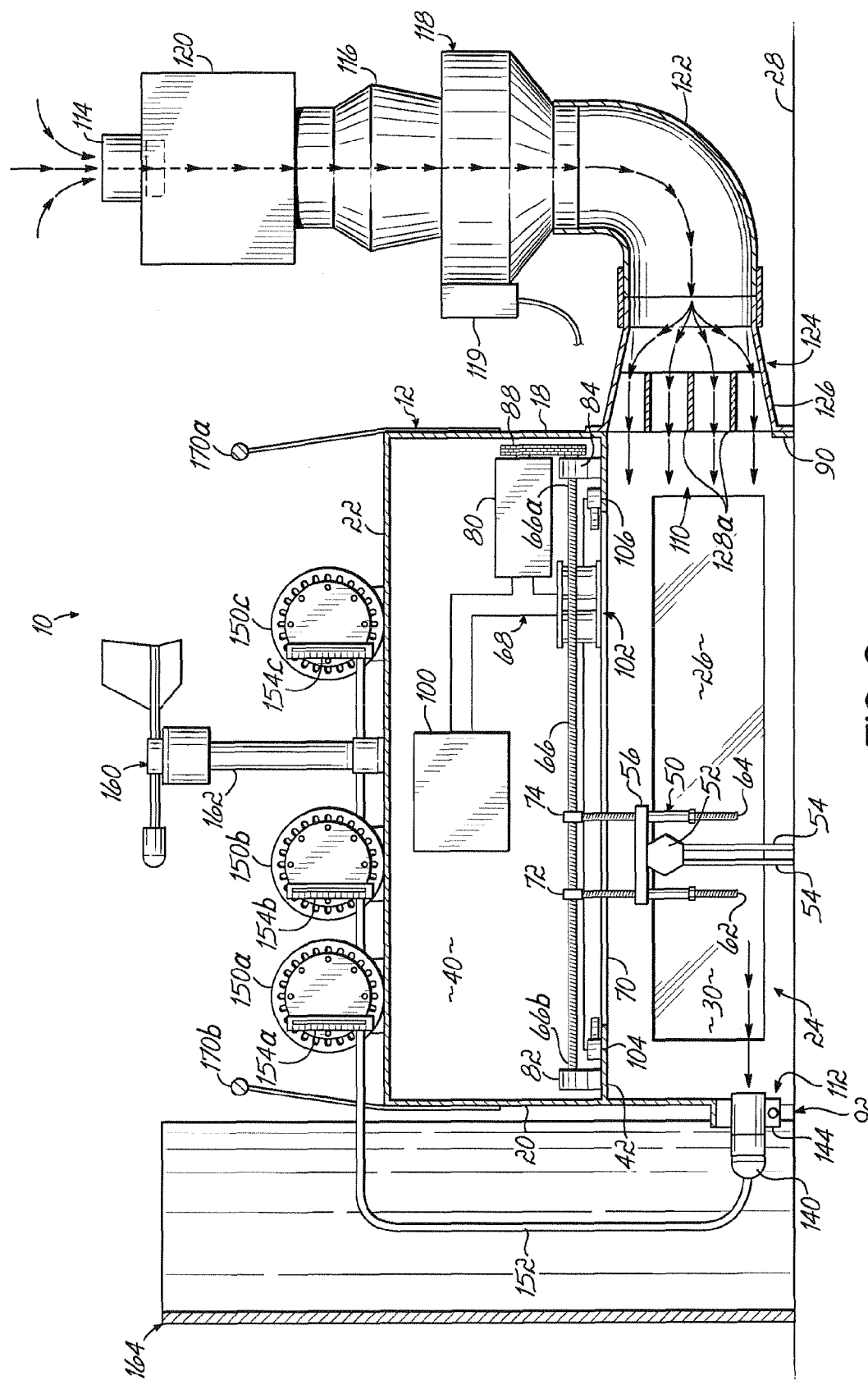
FIG. 2 is a cross-sectional view of the apparatus of FIG. 1.
Figure 3:
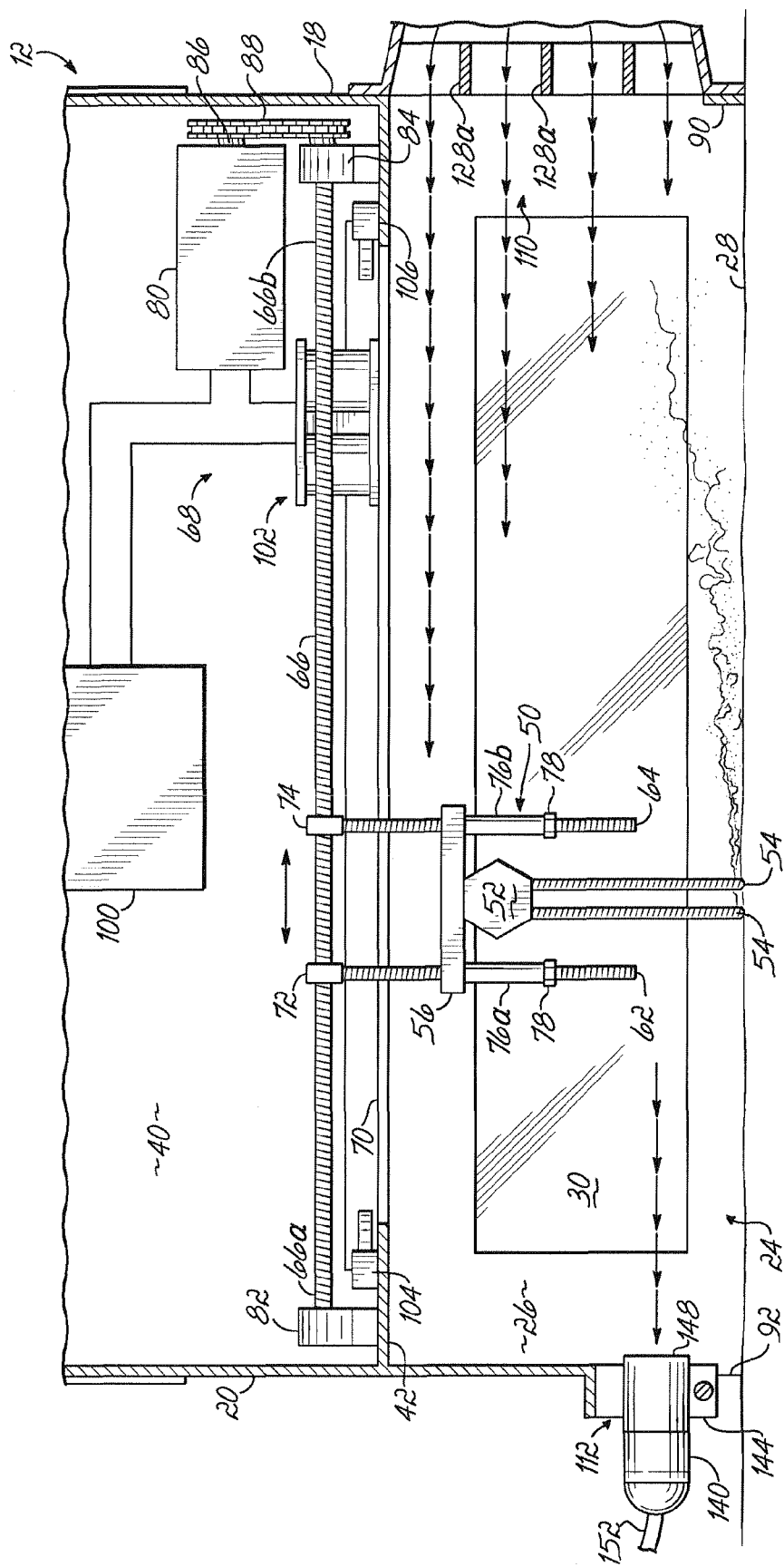
FIG. 3 is an enlarged cross-sectional view, similar to FIG. 2.

FIGS. 1-3 depict an exemplary apparatus 10 for in-situ sampling of airborne material released from a surface, in accordance with the principles of the present disclosure. The apparatus 10 includes a housing 12 having first and second oppositely disposed sidewalls 14, 16, first and second oppositely disposed end walls 18, 20 adjacent the first and second sidewalls 14, 16, and a top wall 22 extending between upper ends of the first and second sidewalls 14, 16 and the first and second end walls 18, 20 to form an enclosure. The housing 12 includes an open end 24 generally opposite the top wall 22. The sidewalls 14, 16 and end walls 18, 20 thereby define a test chamber 26 proximate the open end 24, and the open end 24 is adapted to confront a test surface 28 to expose the test surface 28 to the test chamber 26. The peripheral edges of the housing 12 around the opening 24 may be provided with foam gasket material (not shown), or any other material suitable for substantially isolating the portion of the test surface 28 exposed to the test chamber 26 from the surrounding environment. In one embodiment, the test chamber 26 is approximately 6 inches high and approximately 6 inches wide, and has a length of approximately 24 inches.

In the embodiment shown, the first and second sidewalls 14, 16 include windows 30 positioned adjacent the test chamber 26 to facilitate viewing the interior of the test chamber 26 while the apparatus 10 is in use. With particular reference to FIGS. 2 and 3, the housing 12 further includes an interior compartment 40 disposed between the test chamber 26 and the top wall 22 for enclosing various mechanical and/or electrical components of the sampling apparatus 10, as will be described in more detail below. The boundary of the test chamber 26 and the compartment 40 is defined by an intermediate wall 42 disposed generally parallel to the top wall 22 and positioned between the opening 24 and the top wall 22. The housing 12 of the exemplary embodiment is formed from 0.08 inch-thick anodized aluminum sheet that has been cut, bent, and welded or other wise fastened together to form the various features described herein. It will be appreciated, however, that the housing may be formed from various other materials and by various other methods to obtain an enclosure as described generally herein.

Figure 5:
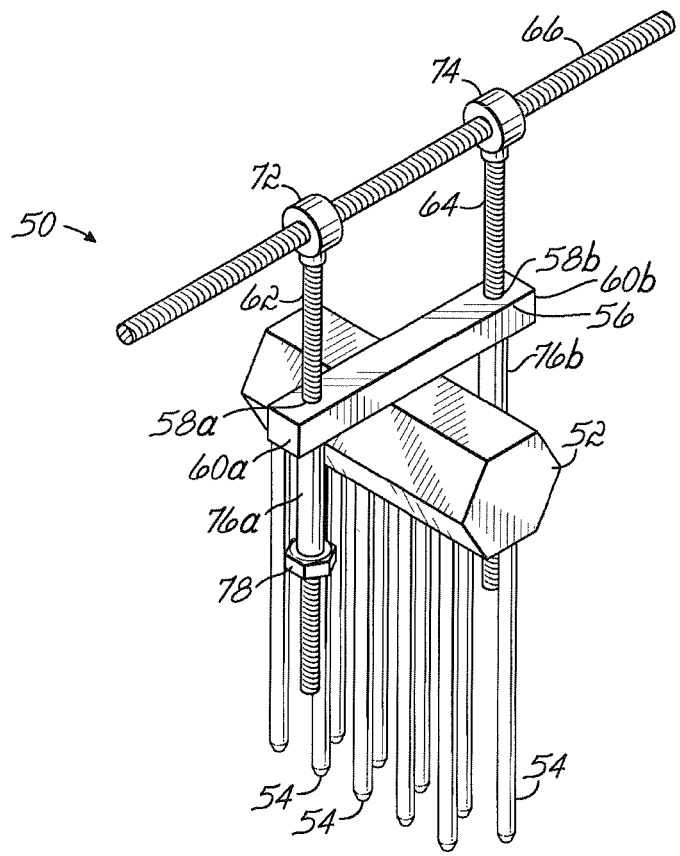
FIG. 5 is a perspective view of an agitator used in the apparatus of FIG. 1.

The apparatus 10 further includes an agitator 50 disposed within the test chamber 26. The agitator 50 is movable within the test chamber 26 and contacts the test surface 28 during movement thereof to thereby disturb the test surface 28 and release material into the air within the test chamber 26. Referring to FIGS. 3 and 5, the agitator 50 includes an agitator block 52 and a plurality of elongate tines 54 extending downwardly from the agitator block 52 to engage the test surface 28. In this embodiment, the agitator 50 includes ten tines 54 that are spaced from one another and arranged in two generally parallel rows. It will be appreciated, however, that the agitator 50 may include various other configurations of tines 54, or various other structure suitable for contacting the test surface 28 to facilitate releasing material into the air within the test chamber 26.

The agitator block 50 is coupled to an elongate yoke 56 having apertures 58a, 58b provided at opposite terminal ends 60a, 60b. The agitator 50 is supported by a pair of vertical rods 62, 64 extending through the apertures 60a, 60b in the yoke 56 and having upper ends operatively coupled to the threaded rod 66 of an actuator assembly 68 disposed in the compartment 40 above the test chamber 26. The vertical rods 62, 64 extend through a generally elongate slot 70 provided in the intermediate wall 42 between the test chamber 26 and the compartment 40. The threaded rod 66 extends generally parallel to the test chamber 26 and the vertical rods 62, 64 are coupled to the threaded rod 66 by bushings 72, 74 that are threadably engaged with the threaded rod 66 such that when the threaded rod 66 is rotated, the bushings 72, 74 are caused to move along the length of the threaded rod 66 thereby imparting movement to the agitator 50 within the test chamber 26. The vertical rods 62, 64 are also threaded and the vertical position of the yoke 56 and agitator block 52 within the test chamber 26 may be adjusted by selectively adjusting the position of sleeves 76a, 76b and nuts 78 provided on the respective vertical rods 62, 64 and supporting the yoke 56 thereon.

The actuator assembly 68 further includes a motor 80, such as gear motor part number 4FM-17 available from W.W. Grainger, Inc. of Lake Forest, Ill., disposed in the compartment 40 and operatively coupled to the threaded rod 66. The ends 66a, 66b of the threaded rod 66 are rotatably supported in bearing blocks 82, 84, such as part number 5912K22 available from McMaster-Carr Supply Co. of Elmhurst, Ill. An output shaft 86 of the motor 80 is coupled to one end of the threaded rod 66 by a drive chain 88, whereby the threaded rod 66 may be rotated about its longitudinal axis by the motor 80 to cause the agitator 50 to move within the test chamber 26 between first and second ends 90, 92 of the test chamber 26. The direction of the agitator 50 is determined by the rotational direction of the threaded rod 66. The apparatus 10 further includes a speed control 100, such as part number 4Z826 available from W.W. Grainger, Inc., communicating with the motor 80 and a current switch 102 operative to change the direction of current provided to the motor 80. Changing the direction of the current, in turn, changes the rotational direction of the motor output shaft 86 and the rotational direction of the threaded rod 66.

The apparatus 10 further includes sensors 104, 106 disposed proximate the respective first and second ends 90, 92 of the test chamber 26 to facilitate changing the direction of motion of the agitator 50 within the test chamber 26. In the embodiment shown, the sensors 104, 106 comprise limit switches, such as part number 6X289 available from W.W. Grainger, Inc., in electrical communication with the current switch 102 and the control 100. As the agitator 50 is driven by the threaded rod 66 toward one of the first and second ends 90, 92 of the test chamber 26, one of the vertical rods 62, 64 will eventually engage one of the sensors 104, 106. In response, the respective sensor 104, 106 sends a signal to the current switch 102 and the control 100 which in turn respond to change the rotational direction of the motor 80 and the threaded rod 66, thereby causing the agitator 50 to move in the opposite direction. The agitator 50 will continue moving in the opposite direction, toward the other end of the test chamber until a threaded rod 90, 92 contacts the other sensor 104, 106, and the direction is again reversed. The agitator will continue moving back and forth between the first and second ends 90, 92 of the test chamber 26 during the collection of a test sample.

While the agitator 50 has been shown and described herein as including tines 54 that are moved in a substantially linear motion, it will be appreciated that the agitator may alternatively comprise various other structure suitable for agitating the surface and/or may utilize various other types of motion, such as rotational motion, non-periodic or random motion, compaction-type motion, or any other type of motion that facilitates the release of material from a test surface 28.

With continued reference to FIGS. 1-3, the test chamber 26 includes an air inlet 110 at the first end 90 of the test chamber 26 for providing a flow of air through the test chamber 26. The air flows over the test surface 28 and exits through an outlet 112 at the second end 92 of the test chamber 26. In the embodiment shown, air is drawn through an air inlet 114 and into an inlet conduit 116 by a fan 118 provided near the first end 90 of the test chamber 26. The air passes through a High Efficiency Particulate Air (HEPA) filter 120, such as part number 506510 available from Labconco Corporation of Kansas City, Mo., to prevent asbestos or other airborne particles outside the apparatus 10 from entering the test chamber 26. The air is directed through an arcuate elbow 122 and a diffuser 124 having tapered sidewalls 126 to the inlet 110 of the test chamber 26. The speed of the fan 118 may be adjustable, such as by a selectively adjustable power supply 119, to vary the flow rate of air through the test chamber 26. In the embodiment shown, the inlet conduit 116 and elbow 122 may be formed from 6-inch diameter PVC pipe, such as reducing coupling part number 4511K86 available from McMaster-Carr Supply Co. and 90-degree elbow part number 1WKV4 available from W.W. Grainger, Inc. The fan 118 may be an in-line centrifugal duct fan, part number 19135K65, available from McMaster-Carr Supply Co.

Figure 4:
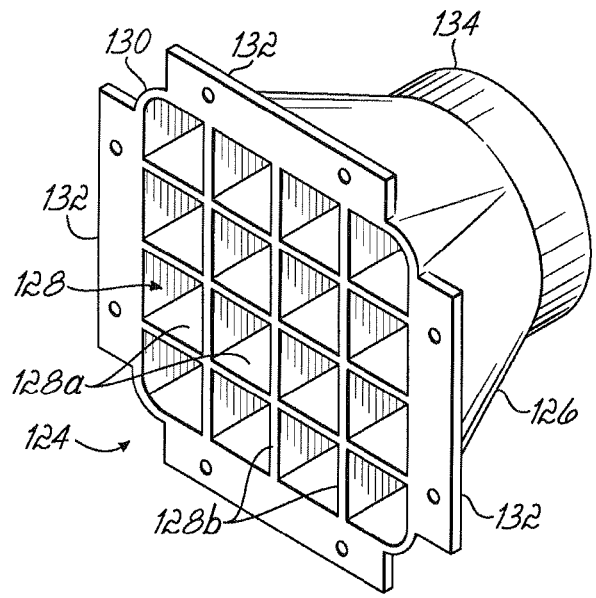
FIG. 4 is a perspective view of a flow diffuser used in the apparatus of FIG. 1.

FIG. 4 depicts the diffuser 124 used in this exemplary embodiment. The diffuser 124 has a generally rectangular first end 130 with mounting flanges 132 for coupling to the first end 90 of the test chamber 26, and a generally circular second end 134 for coupling to the elbow 122. The diffuser 124 includes flow-straightening vanes 128 aligned with a longitudinal direction of the test chamber 26 to create a laminar flow of air through the test chamber 26 from the inlet 110 to the outlet 112. As seen in FIG. 4, the flow straightening vanes 128 are spaced approximately 1.5 inches apart and include a plurality of generally horizontal vanes 128a and a plurality of generally vertical vanes 128b.

Figure 6:
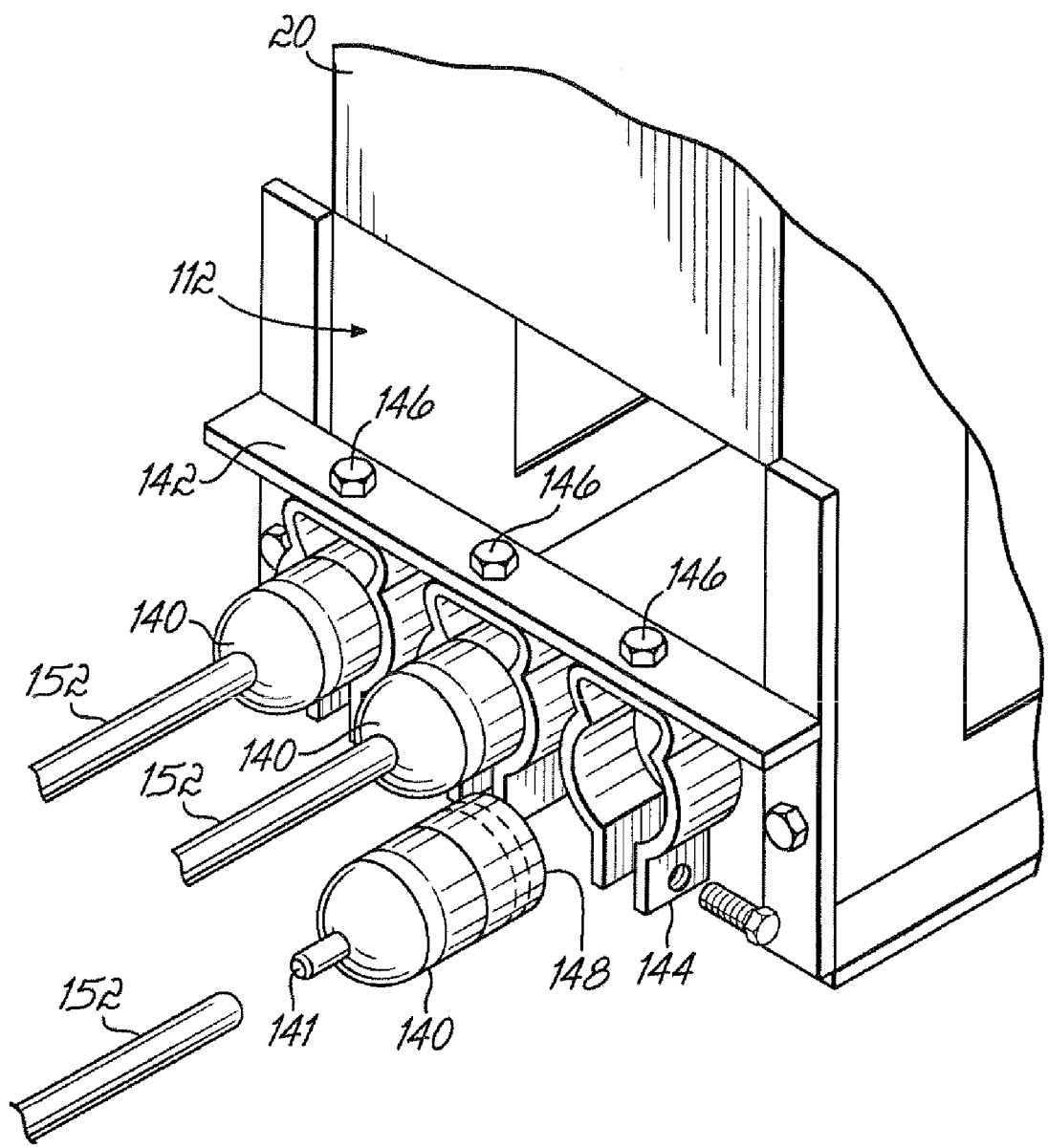
FIG. 6 is a detail perspective view of the air sampling end of the apparatus of FIG. 1.

With particular reference to FIGS. 1, 3, and 6, the outlet 112 at the second end 92 of the test chamber 26 includes a generally rectangular opening formed in the second end wall 20 to permit air flowing through the test chamber 26 to exit the second end 92 of the test chamber 26. One or more sample cassettes 140 are provided adjacent the outlet 112 for collecting samples of the air passing through the outlet 112 of the test chamber 26. In the embodiment shown, three sample cassettes 140 are used to simultaneously collect samples of the air flowing through the outlet 112. The cassettes 140 are supported on a mounting bar 142 extending across the outlet 112 and are held in position by respective clamps 144 attached to the mounting bar 142, by fasteners 146. In the embodiment shown, the sample cassettes 140 are 25 mm-diameter, mixed cellulose ester (MCE) filters having 0.8 μm pore size adapted to collect particulate material in the air flowing through the test chamber 26. An exemplary sample cassette 140 is part number 225-321 available from SKC, Inc. of Eighty-Four, Pa.

The sample cassettes 140 are positioned a distance above the test surface 28 that facilitates collecting airborne material released from the test surface 28. In one embodiment, the sample cassettes 140 may be positioned with their centerlines approximately 1.5 inches above the test surface 28. In this embodiment, two sample cassettes 140 are positioned with their centerlines approximately 1.5 inches from the respective sidewalls 14, 16, and a third sample cassette is positioned with its centerline approximately 3 inches from either sidewall 14, 16. The leading edges 148 of the sample cassettes 140 are positioned approximately 2 inches from the outlet 112. It will be appreciated, however, that various other types and sizes of sample cassettes 140 may alternatively be used and/or the sample cassettes 140 may be positioned and arranged in various other configurations to facilitate collecting samples of the released material from within the test chamber 26.

Each sample cassette 140 is coupled to a respective vacuum pump 150a, 150b, 150c by a vacuum conduit 152. The vacuum pumps 150a, 150b, 150c draw air flowing through the test chamber outlet 112 into the respective sample cassettes 140. In the embodiment shown, the pumps 150a, 150b, 150c are 1/10 HP rotary vane oil-less vacuum pumps, model number 1532-101, available from Gast Manufacturing, Inc. of Benton Harbor, Mich. The pumps 150a, 150b, 150c may be placed on top of the housing 12 to help keep the apparatus 10 stable during test, or may be positioned in various other locations. Each pump 150a, 150b, 150c includes a gauge 154a, 154b, 154c, such as in-line flow control meter part number MMF-24-TMV available from Dwyer Instruments, Inc. of Michigan City, Ind., or any other suitable device for indicating the vacuum pressure developed by each pump 150a, 150b, 150c so that the air flow drawn into the respective sample cassettes 140 may be carefully and uniformly controlled.

In use, the apparatus 10 is positioned directly on a test surface 28 at a desired test site. Before sampling at the desired test location, each of the pumps 150a, 150b, 150c should be calibrated with a representative sample cassette 140. The total sample air volume to be collected will be determined by site conditions and properties of the test matrix. Accordingly, prior to collection of actual samples, trial samples should be collected to determine the maximum air volume that will yield an acceptable filter loading of the sample cassettes 140, as determined by on-site optical examination of the trial sample cassettes 140. In one embodiment, samples may be collected at a target air flow rate of approximately 14 liters-per-minute for a period of approximately 5 to 30 minutes, to achieve a target air volume of approximately 70 to 420 liters. Before the apparatus 10 is placed at the location to be tested, the apparatus 10 should be decontaminated to reduce or eliminate the possibility of cross contamination from previous test sites. After decontaminating the apparatus 10, an equipment blank sample should be collected to demonstrate the cleanliness of the instrument and to ensure that no cross-contamination occurs between samples. The sample site should also be selected to be devoid of vegetation and large rocks. For example, any rock greater than ½ inch in diameter should be removed from the test area.

Prior to conducting a test, the position of the agitator yoke 56 on the vertical rods 62, 64 should be adjusted by rotating the respective nuts 78 on the vertical rods 62, 64 to move the sleeves 76a, 76b to positions that allow the tines 54 of the agitator 50 to freely contact the test surface 28. The apparatus 10 may then be positioned over the test surface 28 with the open end 24 confronting the test surface 28 to expose a portion of the test surface 28 to the test chamber 26. Anchors, such as tent stakes (not shown), may be used to secure the apparatus 10 to the test surface 28. The vacuum pumps 150a, 150b, 150c may also be placed atop the housing 12 to weigh down the apparatus 10 at the test surface 28 and prevent movement of the apparatus 10 during the test.

With the apparatus 10 in place, the sample cassettes 140 may be positioned within their respective clamps 144 and the vacuum conduits 152 may be coupled to the respective sample cassettes 140, such as at outlet tips 141 (FIG. 6). The opposite ends of the vacuum conduits 152 are coupled to the respective vacuum pumps 150a, 150b, 150c. The vacuum pumps 150a, 150b, 150c are started to begin drawing air through the sample cassettes 140 and power is provided to the fan 118 to draw air from the environment through the air inlet 114 of the inlet conduit 116. In one embodiment, the speed of the fan 118 may be adjusted to achieve a flow velocity of approximately 264 to 440 feet per minute within the test chamber 26. The velocity of the air flow within the test chamber 26 may be verified using a hot wire anemometer or any other device suitable for measuring air velocity. Power is then provided to the actuator motor 80 to cause the agitator 50 to move within the test chamber 26 as described above.

As the agitator 50 moves over the test surface 28 to release asbestos or other material into the air flowing through the test chamber 26, the vacuum pumps 150a, 150b, 150c draw air from the test chamber 26 into the sample cassettes 140. At the conclusion of a test, power to the actuator motor 180 is terminated to stop the movement of the agitator 50. Power is then terminated to the fan 118 to stop the flow of air through the test chamber 26, and the pumps 150a, 150b, 150c are then stopped to terminate the collection of air samples by the sample cassettes 140.

In one embodiment, one of the collected sample cassettes 140 may be examined onsite using a phase contrast microscope to determine the quality of the collected sample while the apparatus 10 is still in position on the previously sampled test surface 28. If it is determined that the quality of the collected sample is inadequate, such as if the sample cassette 140 is overloaded, for example, the previously collected samples may be discarded and the test may be conducted using an adjusted flow rate until acceptable samples are obtained.

To facilitate obtaining acceptable samples, the apparatus 10 may further include a wind direction indicator 160 to aid in properly orienting the apparatus 10 with the predominant wind. In the embodiment shown, the wind indicator 160 includes a stand 162 for mounting the device to the housing 12 or other convenient surface. The apparatus 10 may be oriented such that the outlet 112 of the test chamber 26 is in the same direction as the predominant wind at the test site. The apparatus 10 may further include a wind break 164 or other structure which may be placed adjacent the outlet 112 of the test chamber 26, to prevent ambient wind from disturbing the collection of test samples. To facilitate transporting the apparatus 10 and to facilitate positioning the apparatus 10 at a desired test site, handles 170a, 170b may be provided on housing 12, such as adjacent end walls 18, 20, as shown in FIGS. 1 and 2.

While the present invention has been illustrated by the description of an embodiment thereof, and while the embodiment has been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

1. A sampling apparatus, comprising:
    a housing including at least one sidewall defining a test chamber, said test chamber including an opening adapted to confront a test surface and expose at least a portion of the test surface to said test chamber;
    an agitator disposed within said test chamber, said agitator being selectively movable within said test chamber and adapted to contact the test surface during movement thereof;
    an inlet communicating with said test chamber;
    an outlet communicating with said test chamber and open to atmosphere;
    said inlet and said outlet defining an air flow path through said test chamber;
    a support member associated with said outlet and adapted to support at least one sample cassette in the air flow path through said test chamber; and
    a fan communicating with said inlet and providing a flow of air through said test chamber, between said inlet and said outlet.

2. The apparatus of claim 1, wherein said agitator comprises at least one tine adapted to contact the test surface as said agitator is moved within said test chamber.

3. The apparatus of claim 1, further comprising an actuator operatively coupled to said agitator, said actuator adapted to move said agitator along a predefined path within said test chamber.

4. The apparatus of claim 3, further comprising a control in communication with said actuator, said control operative to control said actuator to repeatably move said agitator along said predefined path.

5. The apparatus of claim 3, wherein said actuator includes a threaded rod and a motor operatively coupled to said threaded rod, said motor operable to rotate said threaded rod in opposite angular directions to thereby move said agitator in opposite linear directions within said test chamber.

6. The apparatus of claim 1, further comprising a least one vane proximate said inlet for straightening air flow through said inlet.

7. A sampling apparatus, comprising:
    a housing including at least one sidewall defining a test chamber, said test chamber including an opening adapted to confront a test surface and expose at least a portion of the test surface to said test chamber;
    an agitator disposed within said test chamber, said agitator being selectively movable within said test chamber and adapted to contact the test surface during movement thereof;
    an inlet communicating with said test chamber;
    an outlet communicating with said test chamber;
    said inlet and said outlet defining an air flow path through said test chamber;
    a fan communicating with said inlet and providing a flow of air through said test chamber, between said inlet and said outlet;
    a plurality of sample cassettes positioned in the air flow path through said test chamber; and
    a plurality of pumps, each said pump operatively coupled to a respective one of said sample cassettes for drawing air from said test chamber into said sample cassette.

8. The sampling apparatus of claim 1, further comprising:
    at least one sample cassette coupled to said support member;
    said at least one sample cassette positioned proximate said outlet.

9. The sampling apparatus of claim 7, wherein said plurality of sample cassettes are positioned proximate said outlet.

* * * * *